(12) United States Patent
Chiba (10) Patent No.: US 12,049,641 B2
(45) Date of Patent: Jul. 30, 2024

(54) METHOD FOR HARVESTING CULTURED CELLS FROM THREE-DIMENSIONAL POROUS SCAFFOLD

(71) Applicant: FULLSTEM CO., LTD., Okinawa (JP)

(72) Inventor: Shunmei Chiba, Okinawa (JP)

(73) Assignee: FULLSTEM CO., LTD., Okinawa (JP)

( * ) Notice: Subject to any disclaimer, the term of this patent is extended or adjusted under 35 U.S.C. 154(b) by 474 days.

(21) Appl. No.: 16/328,584

(22) PCT Filed: Dec. 25, 2017

(86) PCT No.: PCT/JP2017/046420
§ 371 (c)(1),
(2) Date: Feb. 26, 2019

(87) PCT Pub. No.: WO2018/123966
PCT Pub. Date: Jul. 5, 2018

(65) Prior Publication Data
US 2021/0207084 A1   Jul. 8, 2021

(30) Foreign Application Priority Data
Dec. 27, 2016  (JP) ................. 2016-252742

(51) Int. Cl.
*C12N 5/0735* (2010.01)
*C12N 5/074* (2010.01)
*C12N 5/0789* (2010.01)

(52) U.S. Cl.
CPC ........ *C12N 5/0606* (2013.01); *C12N 5/0647* (2013.01); *C12N 5/0696* (2013.01); *C12N 2509/10* (2013.01); *C12N 2527/00* (2013.01)

(58) Field of Classification Search
CPC .. C12N 5/0606; C12N 5/0647; C12N 5/0696; C12N 2509/10; C12N 2527/00; C12M 27/16; G01N 27/745
See application file for complete search history.

(56) References Cited

U.S. PATENT DOCUMENTS

| | | | | |
|---|---|---|---|---|
| 7,585,670 B2* | 9/2009 | Hedrick | ............ | A61K 35/28 435/325 |
| 7,754,478 B2* | 7/2010 | Suzuki | ............ | C12M 23/22 435/303.3 |
| 2008/0102478 A1 | 5/2008 | Li et al. | | |
| 2009/0076530 A1 | 3/2009 | Fukutomi et al. | | |
| 2012/0283130 A1 | 11/2012 | Yamanaka et al. | | |
| 2014/0193901 A1 | 7/2014 | Lee et al. | | |
| 2015/0299634 A1 | 10/2015 | Drugmand et al. | | |
| 2017/0073625 A1* | 3/2017 | Kasuto | ............ | C12M 23/34 |

FOREIGN PATENT DOCUMENTS

| | | |
|---|---|---|
| JP | S62-500351 A | 2/1987 |
| JP | 2005-160370 A | 6/2005 |
| JP | 2005-328726 A | 12/2005 |
| JP | 2008-079554 A | 4/2008 |
| JP | 2009-125068 A | 6/2009 |
| JP | 2010-505393 A | 2/2010 |
| JP | 2013-516982 A | 5/2013 |
| JP | 2013-255483 A | 12/2013 |
| JP | 2014-158461 A | 9/2014 |
| JP | 2016-501525 A | 1/2016 |
| JP | 2017-158488 A | 9/2017 |
| WO | WO 1986/01531 A1 | 3/1986 |
| WO | WO 2007/102606 A1 | 9/2007 |
| WO | WO-2012140519 A2 * | 10/2012 ............ C12M 47/02 |

OTHER PUBLICATIONS

Liberase Product Prolife sheet. Data sheet [online]. Roche Cortp. 2020 (retrieved on Aug. 12, 2021 ) from the internet: <URL: www.https://custombiotech.roche.com/home/Product_Details/3_5_3_3_12_5.product-classes%5CEnzymes%5Cproteases.html>.*
Bollaro et al ("Comparison of Skeletal Muscle Monolayer Cultures Initiated With Cells Dissociated By the Vortex and Trypsin Methods," In Vitro 12(8): 564-570, 1976) (Year: 1976).*
Dusting et al ("Flows Within a Cylindrical Cell Culture Bioreactor with a Free-Surface and a Rotating Base," 15th Australasian Fluid Mechanics Conference, Dec. 13-17, 2004) (Year: 2004).*
Fullstem Co., Ltd., Applicant's Reply to IPEA's Dec. 11, 2018 International Preliminary Report on Patentability for International Application No. PCT/JP2017/046420, Dec. 11, 2018, 21 pages, Maeda & Partners, Japan.
International Preliminary Examining Authority (IPEA), International Preliminary Report on Patentability for International Application No. PCT/JP2017/046420, Dec. 11, 2018, 7 pages, Japan Patent Office, Japan.
International Searching Authority (ISA), International Search Report (ISR) and Written Opinion for International Application No. PCT/JP2017/046420, Apr. 3, 2018, 10 pages, Japan Patent Office, Japan.
Montanaro, Federica, et al., "Demystifying SP cell purification: viability, yield, and phenotype are defined by isolation parameters", *Experimental Cell Research*, 2004, p. 144-154 vol. 298, Elsevier, Inc., US.

(Continued)

*Primary Examiner* — Emily A Cordas
(74) *Attorney, Agent, or Firm* — Alston & Bird LLP (57) ABSTRACT

Provided is a method for efficiently harvesting cells cultured at a large scale from a three-dimensional porous scaffold. This method includes: a culturing step in which cells are cultured on a three-dimensional porous scaffold sealed in a culture vessel; an enzymatic treatment step in which an enzyme solution containing trypsin-EDTA, caseinase, and/or collagenase is added to the culture vessel to conduct an enzymatic treatment on the cultured cells in the culture vessel; and a vibration treatment step in which a vibration treatment is conducted, i.e., a base that makes a circular motion within a horizontal plane and a bottom surface of the culture vessel are made to come into surface contact with one another so as to impart a vertical-direction vibration to the cultured cells that have undergone the enzymatic treatment.

11 Claims, 7 Drawing Sheets

(56) References Cited

OTHER PUBLICATIONS

Worthington Biochemical Corporation, "Worthington Tissue Dissociation Guide, Dissociating Enzymes: Collagenase", 2 pages, retrieved from <http://www.worthington-biochem.com/tissuedissociation/collagenase.html> Feb. 25, 2019.

* cited by examiner

METHOD FOR HARVESTING CULTURED CELLS FROM THREE-DIMENSIONAL POROUS SCAFFOLD

CROSS REFERENCE TO RELATED APPLICATIONS

This application is a national stage application, filed under 35 U.S.C. § 371, of International Application No. PCT/JP2017/046420, filed Dec. 25, 2017, which International Applications claims priority to and the benefit of Japanese Application No. 2016-252742, filed Dec. 27, 2016, the contents of both of which as are hereby incorporated by reference in their entirety.

BACKGROUND

Technical Field

The present invention relates to a method for harvesting cultured cells from a three-dimensional porous scaffold, and more particularly, to a method for efficiently harvesting a large amount of cultured cells from a three-dimensional porous scaffold having a large culture area.

Description of Related Art

Pluripotent stem cells (embryonic stem cells, induced pluripotent stem (iPS) cells) have been acknowledged as important cell sources for regenerative medicine due to their unlimited proliferative capacity and pluripotency. The iPS cell technology has recently been studied and developed worldwide because it is applicable to elucidation of pathological conditions due to the establishment of drug toxicity tests and establishment of disease models. For the application of use of such pluripotent stem cells to the regenerative medicine and drug discovery studies, it is indispensable to stably supply a large amount of undifferentiated cells and differentiated cells.

A method of culturing cells in a monolayer on a plate is called two-dimensional culture, whereas a technique of culturing cells in a structure having a vertical thickness is called three-dimensional culture. Since three-dimensional culture is closer to the state of cells in vivo than two-dimensional culture is, the three-dimensional culture is not only suitable for establishing an experimental model simulating an in-vivo environment, but also capable of achieving cell culture in large scale.

Patent Document 1 discloses a three-dimensional porous scaffold (in the present specification, the scaffold may also be referred to as a "matrix") including an aggregate of biocompatible polymeric fibers having a predetermined diameter and an apparent density, as well as a cell culture method using the three-dimensional porous scaffold.

Patent Document 2 describes a cell culture method in which a three-dimensional porous scaffold inoculated with cells is placed in a sealable cell culture vessel, and pressure is applied to the three-dimensional porous scaffold by a piston so as to cause compressive deformation in the three-dimensional porous scaffold.

Patent Document 3 discloses a three-dimensional porous scaffold inoculated with cells, and a cell culture method which allows a microfluid to flow through a microfluidic channel extending over a surface of the three-dimensional porous scaffold.

Patent Document 1: Domestic Re-Publication of PCT International Publication No. 2007/102606

Patent Document 2: Japanese Unexamined Patent Publication No. 2009-125068.

Patent Document 3: Japanese Unexamined Patent Publication (Japanese Translation of PCT International Application) No. 2010-505393

BRIEF SUMMARY

While a large amount of cells can be cultured in the three-dimensional porous scaffold described above, it is difficult to efficiently harvest cultured cells from the scaffold. In particular, it is significantly difficult to harvest cultured cells that are deeply buried in the three-dimensional porous scaffold with efficiency while avoiding damage to the cultured cells.

It is therefore an object of the present invention to provide a method for harvesting cultured cells from a three-dimensional porous scaffold with efficiency while avoiding damage to the cultured cells.

A method for harvesting cultured cells according to the present invention includes the steps of: culturing cells in a three-dimensional porous scaffold sealed in a culture vessel; providing an enzyme treatment on the cultured cells in the culture vessel, the enzyme treatment performed by adding an enzyme solution containing trypsin-EDTA and caseinase into the culture vessel; and providing a vibration treatment on the cultured cells, the vibration treatment performed by bringing the culture vessel into surface contact with a platform making a circular motion in a horizontal plane so that a vertical vibration is applied to the cultured cells subjected to the enzyme treatment.

The present invention makes it possible to harvest cultured cells from a three-dimensional porous scaffold with efficiency while avoiding damage to the cultured cells.

DETAILED DESCRIPTION OF VARIOUS EMBODIMENTS

Embodiments of the present invention will be described in detail below with reference to the accompanying drawings. It should be noted that the embodiments are intended to facilitate understanding of the principles of the present invention, and the scope of the present invention is not limited to the following embodiments. Other embodiments, in which a configuration of the following embodiments is appropriately replaced by those skilled in the art, are also encompassed in the scope of the present invention.

A cultured cell harvesting method according to this embodiment includes a culture step of culturing cells, an enzyme treatment step of providing an enzyme treatment on the cultured cell, and a vibration treatment step of providing a vibration treatment by applying a vibration to the cultured cells.

In the culture step, cells are cultured in a three-dimensional porous scaffold sealed in a culture vessel. The cells to be cultured are not limited to any particular cells, and may be those cells susceptible or not susceptible to cell injury, wherein cells susceptible to cell injury are preferable. Examples of such cells include human embryonic stem (ES) cells, iPS cells, and adult stem cells (such as mesenchymal stem cells derived from fat or bone marrow).

The culture vessel for culturing cells is a non-cell-adhesive container, whose inner wall is less likely to allow cultured cells to adhere. The culture vessel is made of plastic having low adhesiveness, such as polyethylene terephthalate, polypropylene, polyethylene, polycarbonate, and polystyrene, or is made of plastic or glass subjected to a hydrophobic surface treatment, such as a fluorine treatment and a silicon treatment.

The size and shape of the culture vessel are not particularly limited, and may be selected, according to the cells to be cultured, from a bottle shape, a flask shape, a bag shape, a well shape, a dish shape, and the like, among which the bottle shape is preferable. For example, the culture vessel may have the shape of a bottle whose bottom surface is flat. Alternatively, the culture vessel may have, as a whole, the shape of a substantial cylinder as viewed externally, wherein the bottom surface is flat. Examples of the culture vessel, which is, as a whole, in a substantially cylindrical shape as viewed externally and which has a flat bottom surface, include a culture vessel having a volume of 250 ml (39 mm in mouth diameter, 117 mm in height, and 72 mm in bottom diameter), a culture vessel having a volume of 500 ml (39 mm in mouth diameter, 137 mm in height, and 92 mm in bottom diameter), and a culture vessel having a volume of 1000 ml (39 mm in mouth diameter, 156 mm in height, and 107 mm in bottom diameter).

The three-dimensional porous scaffold may be either a single scaffold or an aggregate of a plurality of scaffolds. The culture area of the three-dimensional porous scaffold is not particularly limited, and may be, for example, 800 $cm^2$ to 900000 $cm^2$, and preferably 800 $cm^2$ to 45000 $cm^2$. The three-dimensional porous scaffold has, for example, an average porosity of 50% to 90%, preferably 80% to 90%, and an average pore size of 10 µm to 800 µm, preferably 200 µm to 400 µm.

For example, the three-dimensional porous scaffold may be a fiber aggregate (e.g., nonwoven fabric, woven fabric, knitted fabric, or the like) made of thermoplastic resin fibers, or a sheet (e.g., a film, a plate, a board, or the like) manufactured through molding a thermoplastic resin that has been kneaded in advance. Examples of the thermoplastic resin include polyglycolic acid, polylactic acid, polylactic acid-polyglycolic acid copolymer, polycaprolactone, polydioxanone, poly(trimethylene carbonate), polybutylene succinate, and polyethylene succinate.

The culture period is not particularly limited, and can be appropriately selected depending on the type of cells, the number of cells to be inoculated, and the like. For example, the culture period is 5 to 30 days following the inoculation of the cells. A normal culture period may be, for example, 5 to 14 days, preferably 7 to 10 days. A long culture period may be, for example, 15 to 30 days, preferably 22 to 26 days.

In the subsequent enzyme treatment step, an enzyme solution containing trypsin-EDTA (hereinafter, sometimes denoted by "T") and at least one of caseinase (hereinafter, sometimes denoted by "D") or collagenase (hereinafter, sometimes denoted by "C") is added into the culture vessel so as to provide an enzyme treatment on the cultured cells in the culture vessel. The EDTA content in the trypsin-EDTA is not particularly limited, and for instance, 4.0-12.0 mmol/L EDTA may be contained with respect to 1.0 w/v % trypsin. For example, the trypsin-EDTA may contain: 0.05 w/v % trypsin and 0.53 mmol/L EDTA; 0.25 w/v % trypsin and 1.0 mmol/L EDTA; or 0.5 w/v % trypsin and 5.3 mmol/L EDTA.

The collagenase is not particularly limited, and examples thereof include the matrix metalloproteinase (MMP) family including MMPs 1, 2, 3, 9, 13, and 14.

In a case where the enzyme solution contains both of trypsin-EDTA and caseinase, the mixing ratio is not particularly limited as long as the enzyme treatment is possible. For example, the enzyme solution has a mixing ratio expressed as trypsin-EDTA:caseinase=0.5 to 4:1 to 2, preferably 2:1.

Here, trypsin-EDTA as purchased is at a concentration of 0.5 mg/ml, and caseinase as purchased contains 1000 units (1 mg/ml=300 units). Thus, the ratio expressed as trypsin-EDTA:caseinase=2:1 refers to a mixture of 1.0 mg/ml trypsin-EDTA and 3.334 mg/ml caseinase.

In a case where the enzyme solution contains both of trypsin-EDTA and collagenase, the mixing ratio is not particularly limited as long as the enzyme treatment is possible. For example, the enzyme solution has a mixing ratio expressed as trypsin-EDTA:collagenase=0.5 to 4:1 to 4, preferably 2:1. Here, trypsin-EDTA as purchased is at a concentration of 0.5 mg/ml, and collagenase as purchased contains 300 units (1 mg/ml=300 units).

In a case where the enzyme solution contains all of trypsin-EDTA, collagenase, and caseinase, the mixing ratio is not particularly limited as long as the enzyme treatment is possible. For example, the enzyme solution has a mixing ratio expressed as trypsin-EDTA:collagenase:caseinase=0.5 to 4:1 to 6:1 to 6. In the case of the normal culture period, the ratio T:C:D is, for example, 0.5 to 2:1 to 2:1 to 2, preferably 2:1:1. In the case of the long culture period, the ratio T:C:D is, for example, 2 to 4:1 to 6:2 to 6, preferably 2:4:4. The long culture period may result in production of a new extracellular matrix around cells due to proliferation of the cells. The extracellular matrix thus produced makes it difficult to harvest the cells. In view of this, the present inventor has conducted studies on the mixing ratio of the enzyme solution for use in the enzyme treatment step as will be shown in the following Examples, and consequently, has made it possible to easily harvest the cells even in the case of a long culture period. Here, trypsin-EDTA as purchased is at a concentration of 0.5 mg/ml, collagenase as purchased contains 300 units (1 mg/ml=300 units), and caseinase as purchased contains 1000 units (1 mg/ml=300 units).

Note that in a case in which the three-dimensional porous scaffold is an aggregate of a plurality of scaffolds, the amount of the solution in the culture vessel may be set to be 1 ml with respect to 10 scaffolds.

The conditions for the enzyme treatment are not particularly limited. For example, the enzyme treatment may be performed for 10 to 30 minutes at 36° C. to 38° C., and preferably for 15 minutes at 37° C.

Note that the enzyme solution may further contain a protease, such as deoxyribonuclease (DNase), papain, elastase, hyaluronidase, chymotrypsin or pronase.

In the subsequent vibration treatment step, a platform that is making a circular motion in a horizontal plane and the bottom surface of the culture vessel into which the enzyme solution has been added are brought into surface contact with each other, so that a vertical vibration is applied to the cultured cells subjected to the enzyme treatment, thereby performing a vibration treatment.

The circular motion is preferably a uniform circular motion, the frequency of which is, for example, 20 Hz to 100 Hz, preferably 40 Hz to 70 Hz. The shape of the platform is not particularly limited, and may be, for example, a plate shape, a bowl shape, etc. The platform that makes the circular motion in the horizontal plane can be a rubber platform provided on an upper portion of a vortex mixer (hereinafter, sometimes denoted by "V"), for example. In the case of a plate-shaped platform, a projection may be provided on an upper portion of the platform. A recess which fits closely to the projection can be provided on the flat bottom surface of a bottle-shaped culture vessel. The circular motion of the platform is properly transmitted to the culture vessel when the platform is making the circular motion in the horizontal plane while the projection on the upper portion of the platform is inserted and closely fitted in the recess in the bottom of the bottle-shaped culture vessel, and while the top surface of the platform and the bottom surface of the culture vessel are in surface contact with each other. Also in the case of a bowl-shaped platform, a projection may be provided on an upper portion of the platform, and a recess which fits closely to the projection may be provided in the bottom surface of the culture vessel. Note that a vortex mixer is a laboratory instrument configured to rotate the bottom of a vessel at a high speed to stir liquid in the vessel, and is comprised of an upward facing electric motor and a rubber platform attached to the electric motor, the rubber platform being at a position offset with respect to the center of the drive shaft of the electric motor.

The culture vessel can be placed with its bottom being in close contact with the platform, or can be placed upside down such that its lid provided at an upper portion of the vessel is in close contact with the platform. Further, it is also possible to hold the culture vessel between a fixing member and a platform that is making a circular motion in a horizontal plane, in a state where the culture vessel being upside down has the bottom and the lid being in contact with the platform and the fixing member, respectively.

In the culture vessel in contact with the platform that is making a circular motion in a horizontal plane, a vertical vibration is applied to the cultured cells, for conceivable reasons as follows. For example, when a cylindrical culture vessel having a flat bottom surface is placed on a platform of a vortex mixer and a vibration is applied to the culture vessel, the platform of the vortex mixer is performing a uniform circular motion, and a horizontal vibration is transmitted to the enzyme solution in a lower portion of the vessel. Due to the horizontal vibration of the bottom of the vessel, the enzyme solution in the vessel collides with the inner wall of the vessel, moves vertically upward, and then moves vertically downward by gravity. Repetition of these movements causes the enzyme solution in the vessel to move vertically upward and downward in a repeated manner. The movements of the enzyme solution in the vessel are transmitted to the three-dimensional porous scaffold in the vessel, resulting in application of a vertical vibration to the cultured cells. Note that in a case where the bottom surface has a conical shape, the liquid in the vessel is stirred in a swirling manner, and hence the matrix also moves along with the swirling flow of the liquid, so that no vertical movement occurs. Further, when a swirling flow is generated in the vessel, the three-dimensional porous scaffold in the vessel floats to an upper portion of the enzyme solution and stays in the vicinity of the center of the swirling flow, which makes it difficult for the vibration to be transmitted to the three-dimensional porous scaffold. It is thus preferable to minimize the occurrence of a swirling flow in the vibration treatment step.

A period for the vibration treatment is not particularly limited. For example, the period may be set to be 10 seconds to 30 minutes.

In the vibration treatment step, pipetting (hereinafter sometimes denoted by "P"), by which the enzyme solution containing the cultured cells is repeatedly sucked into and discharged from a nozzle, may be performed to provide the vibration treatment so as to apply a vibration to the cultured cells.

According to the cultured cell harvesting method of this embodiment, a 500 ml bottle, for example, is used as a culture vessel, and a three-dimensional porous scaffold having a total culture area of, for example, 34000 $cm^2$ is sealed in the culture vessel, in which, for example, 1×10⁹ human adipose tissue-derived mesenchymal cells can be placed. The enzyme treatment and the vibration treatment provided after the culturing make it possible to harvest even cells located deep in the three-dimensional porous scaffold from the three-dimensional porous scaffold with efficiency. Furthermore, according to this embodiment of the present invention, the cells can be harvested with efficiency and at high viability, as shown in the following Examples. Provision of a plurality of culture vessels or use of a culture vessel having an increased internal volume will allow much more cells to be cultured and harvested, and the present invention will provide huge benefits.

EXAMPLES (1) Example 1

The cultured cell harvesting method according to Example 1 is compared with a cultured cell harvesting method according to a comparative example in which neither an enzyme treatment nor a vibration treatment is provided.

Subcutaneous adipose tissues were aseptically collected from an abdominal area of a subject who had agreed to the collection of the tissues. The adipose tissues were treated with collagenase so that cells were dispersed. The cells were then centrifuged, thereby collecting SVF (Stromal Vascular Fraction). After a wash of the SVF with PBS (−), the cells were suspended in a serum-free medium intended for primary culture and obtained by adding, to DMEM/F12, 20 μg/ml reduced glutathione, 5 μg/ml fibronectin, and 100 nM ecotin. The cells were then inoculated into a T flask, and cultured under the conditions of 37° C./5% $CO_2$ until 95% confluence was reached.

Thereafter, the cells were released using a release agent and collected. Following a wash with PBS (−), the cells were suspended in a serum-free medium intended for subculture and obtained by adding 20 μg/ml reduced glutathione to DMEM/F12. The cells were then inoculated into a T flask, and cultured under the conditions of 37° C./5% $CO_2$. This subculture process was repeated to obtain $1\times10^8$ human adipose tissue-derived mesenchymal cells.

The cell culture was carried out using a high-density cell culture system "BelloCell" manufactured by CESCO BIO-ENGINEERING CO., LTD. One disposable culture bottle "BelloCell-500" contained 900 matrices "BioNOC II." The volume of the bottle was 500 ml (39 mm in mouth diameter, 137 mm in height, and 92 mm in bottom diameter). The surface area of all the matrices in one bottle was 15,600 $cm^2$. In the bottle, $1\times10^7$ human adipose tissue-derived mesenchymal cells were placed. Up and down movements of the intra-device elevators of the BelloCell system caused the level of the medium in the BelloCell bottle to rise and descend, which allowed the aeration and nutrition for the cells and the excretion of the metabolites ($CO_2$). The cells were cultured in the bottle for 7 days following the inoculation. Then, PBS (−) was added for a wash.

The PBS (−) was removed. An enzyme solution in a minimum amount required to make all the matrices covered under the solution was added and an enzyme treatment was performed for 15 minutes at 37° C. The enzyme solution was a mixture of trypsin-EDTA and caseinase. The enzyme solution had a mixing ratio expressed as trypsin-EDTA: caseinase=2:1 (T2D1). The amount of the liquid contained in the bottle was 90 ml.

Thereafter, a vibration treatment was provided with use of a vortex mixer (at 2,800-3,200 rpm, for 10 seconds, with the vessel bottom surface kept in contact with the mixer). Specifically, the BelloCell bottle containing the cells subjected to the enzyme treatment was placed on a rubber platform of the vortex mixer, and a vertical vibration was applied to the enzyme-treated cultured cells, thereby performing a vibration treatment. Thereafter, the bottle was gently shaken in a vertical direction manually, and another vibration treatment was provided using the vortex mixer (at 2,800-3,200 rpm, for 10 seconds, with the vessel bottom surface kept in contact with the mixer).

Next, following a wash of the matrices in the bottle with PBS (−), $1\times10^8$ human adipose tissue-derived mesenchymal cells released from the matrices were harvested.

Figure 1:
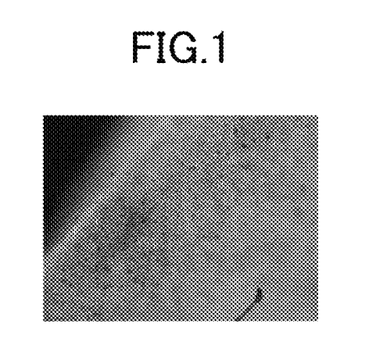
FIG. 1 is a photograph of a matrix from which cells were harvested by a cultured cell harvesting method according to Example 1, wherein an enzyme solution had a mixing ratio expressed as trypsin-EDTA:caseinase=2:1.

The matrices from which the human adipose tissue-derived mesenchymal cells had been released were stained and photographed. The staining was carried out in such a manner that the cells were fixed with 4% paraformaldehyde and then stained with 5 mg/ml crystal violet. After excess crystal violet was washed away, the matrices were dried. The crystal violet was eluted with a 2% SDS solution, followed by photographing. The results are shown in FIG. 1. Note that the viability of the cells was 97.6%.

The large amount of human adipose tissue-derived mesenchymal cells that had been released and was in the form of a cell-suspended solution was made to pass through a 20 μm filter (where 20 μm is larger than the cell diameter and smaller than foreign debris), and the cell-suspended solution was collected and placed into four 50 ml centrifuge tubes.

A medium in an equal amount to the cell-suspended solution in each centrifuge tube was added and the resultant mixture was centrifuged under the conditions of a centrifugal force of 400 g, 5 minutes, and 4° C. The supernatant was discarded in order to obtain a cell pellet.

The human adipose tissue-derived mesenchymal cells were suspended and floated in 20 ml of a medium.

In a 50 ml centrifuge tube, the cell-suspended solution was gently added on top of, thus layered on, a sucrose solution having a specific gravity of 1.20. Note that the human adipose tissue-derived mesenchymal cells had a specific gravity of 1.075 and the foreign debris had a specific gravity of 1.36.

In that state, the content in the centrifuge tube was centrifuged under the conditions of a centrifugal force of 400 g, 10 minutes, and 4° C. The foreign debris having a greater specific gravity precipitated in the sucrose solution and a lowermost portion of the centrifuge tube. The human adipose tissue-derived mesenchymal cells formed a cell layer above the sucrose solution.

The cell layer was solely collected and placed in a 50 ml centrifuge tube, and a medium in an amount greater than or equal to the amount of the cell layer was added thereto. The resultant mixture was centrifuged under the conditions of a centrifugal force of 400 g, 5 minutes, and 4° C., so as to form a cell pellet, which was then re-suspended in a necessary amount of a medium and physiological saline, thereby preparing a cell-suspended solution.

Figure 2:
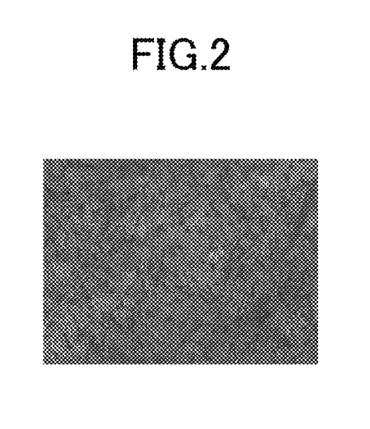
FIG. 2 is a photograph of a matrix from which cells were harvested by a cultured cell harvesting method according to a comparative example.

Next, as a comparative example, cells were cultured in a bottle using the high-density cell culture system "BelloCell" of CESCO BIOENGINEERING CO., LTD., and then PBS (−) was added for a wash, in the same manner as described above. The matrices were stained with crystal violet and then photographed, without being subjected to the enzyme treatment and the vibration treatment. The results are shown in FIG. 2. It has been demonstrated that the cultured cell harvesting method of this Example enables the cells to be harvested with efficiency.

(2) Example 2

In Example 2, studies were made on the enzyme solution for use in the enzyme treatment step.

Similarly to Example 1, cells were cultured in a bottle for 7 days following the inoculation, with use of the high-density cell culture system "BelloCell" of CESCO BIOENGINEERING CO., LTD. Then, PBS (−) was added for a wash.

The PBS (−) was removed. An enzyme solution in a minimum amount required to make all the matrices covered under the solution was added and an enzyme treatment was performed for 15 minutes at 37° C. The enzyme solution was a mixture of trypsin-EDTA, collagenase, and caseinase. The enzyme solution had a mixing ratio expressed as trypsin-EDTA:collagenase:caseinase=2:1:1 (T2C1D1).

Thereafter, similarly to Example 1, a vibration treatment was provided using a vortex mixer (at 2,800-3,200 rpm, for 10 seconds, with the vessel bottom surface kept in contact with the mixer).

Figure 3:
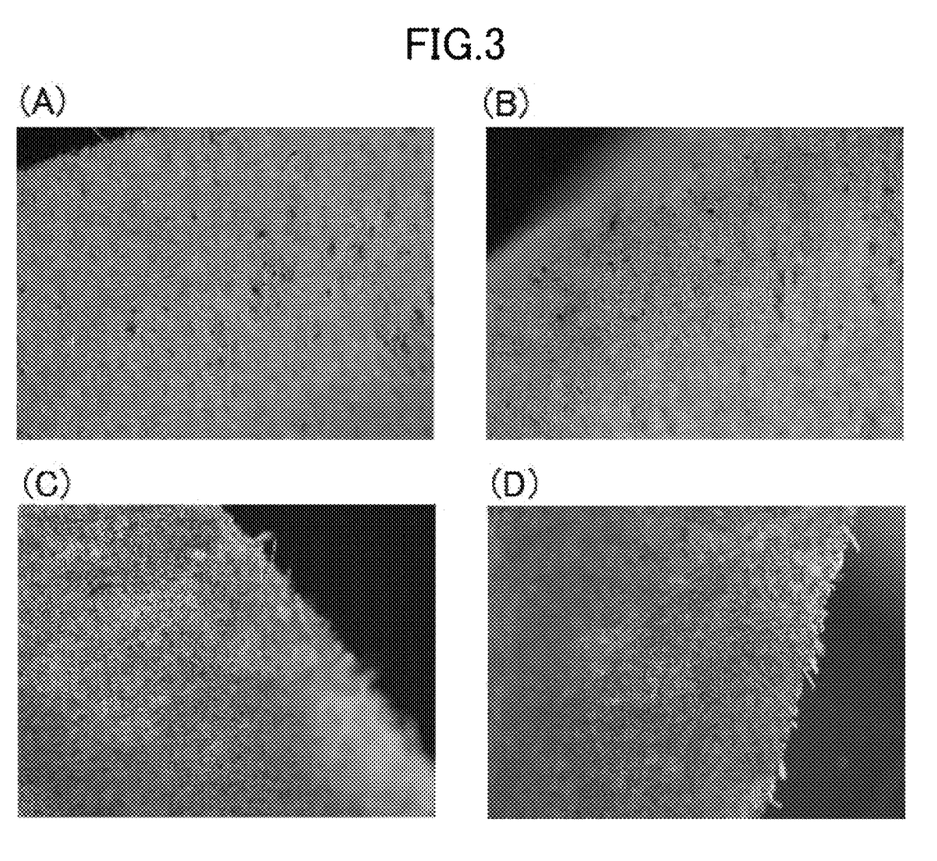
FIG. 3 contains photographs that each show a matrix from which cells were harvested by a cultured cell harvesting method according to Example 2. Photograph (A) shows a case where an enzyme solution had a mixing ratio expressed as trypsin-EDTA:collagenase:caseinase=2:1:1. Photograph (B) shows a case where an enzyme solution had a mixing ratio expressed as trypsin-EDTA:collagenase=2:1. Photograph (C) shows a case where an enzyme solution had a mixing ratio expressed as collagenase:caseinase=1:1. Photograph (D) shows a comparative example.

Following a subsequent wash of the matrices in the bottle with PBS (−), the human adipose tissue-derived mesenchymal cells released from the matrices were harvested. The matrices were stained with crystal violet, in the same manner as in Example 1, and photographed (FIG. 3(A)). Note that the viability of the cells was 98.5%.

The treatments were performed in the same manner as described above except that an enzyme solution used in the enzyme treatment step had a mixing ratio expressed as trypsin-EDTA:collagenase=2:1 (T2C1). The matrices were then photographed (FIG. 3(B)). Note that the viability of the cells was 96.9%.

The treatments were performed in the same manner as described above except that an enzyme solution used in the enzyme treatment step had a mixing ratio expressed as collagenase:caseinase=1:1 (C1D1). The matrices were then photographed (FIG. 3(C)). Note that the viability of the cells was 93.2%.

As a comparative example, cells were cultured in a bottle using the high-density cell culture system "BelloCell" of CESCO BIOENGINEERING CO., LTD., and then PBS (−) was added for a wash, in the same manner as in Example 1. Without being subjected to the enzyme treatment and the vibration treatment, the matrices were stained with crystal violet, and then photographed (FIG. 3(D)).

Figure 4:
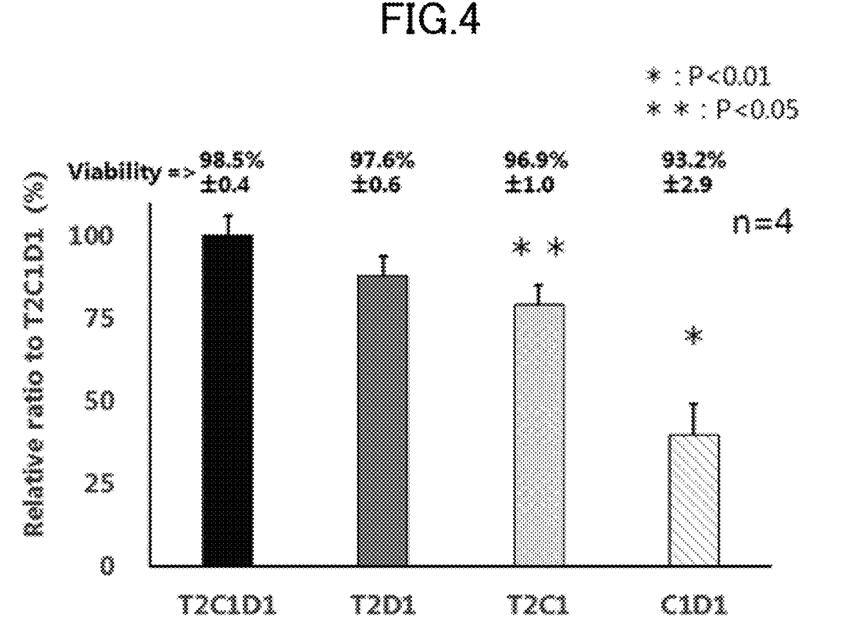
FIG. 4 shows a comparison between cell harvest rates resulting from enzyme solutions containing different ingredients.

Reference is now made to FIG. 4 that shows a comparison between cell harvest rates resulting from enzyme solutions having different ingredients. In FIG. 4, the cell harvest rates are indicated by a relative value while the cell harvest in the case of an enzyme solution of T2C1D1 is assumed to be 100.

The results of Example 1 and Example 2 have demonstrated that the enzyme solution for use in the enzyme treatment needs to contain trypsin-EDTA and at least one of collagenase or caseinase, and that cells can be harvested more efficiently when the enzyme solution contains trypsin-EDTA, collagenase, and caseinase.

(3) Example 3

In Example 3, studies were made on the mixing ratio of the enzyme solution that exhibits the highest harvest efficiency in the case of a normal culture period, that is, on a mixture of trypsin-EDTA, collagenase, and caseinase.

Similarly to Example 1, cells were cultured in a bottle for 7 days following the inoculation, with use of the high-density cell culture system "BelloCell" of CESCO BIOENGINEERING CO., LTD. Then, PBS (−) was added for a wash.

The PBS (−) was removed. An enzyme solution in a minimum amount required to make all the matrices covered under the solution was added and an enzyme treatment was performed for 15 minutes at 37° C. The enzyme solution had a mixing ratio expressed as trypsin-EDTA:collagenase:caseinase=2:2:2 (T2C2D2).

Thereafter, similarly to Example 1, a vibration treatment was provided using a vortex mixer (at 2,800-3,200 rpm, for 10 seconds, with the vessel bottom surface kept in contact with the mixer).

Figure 5:
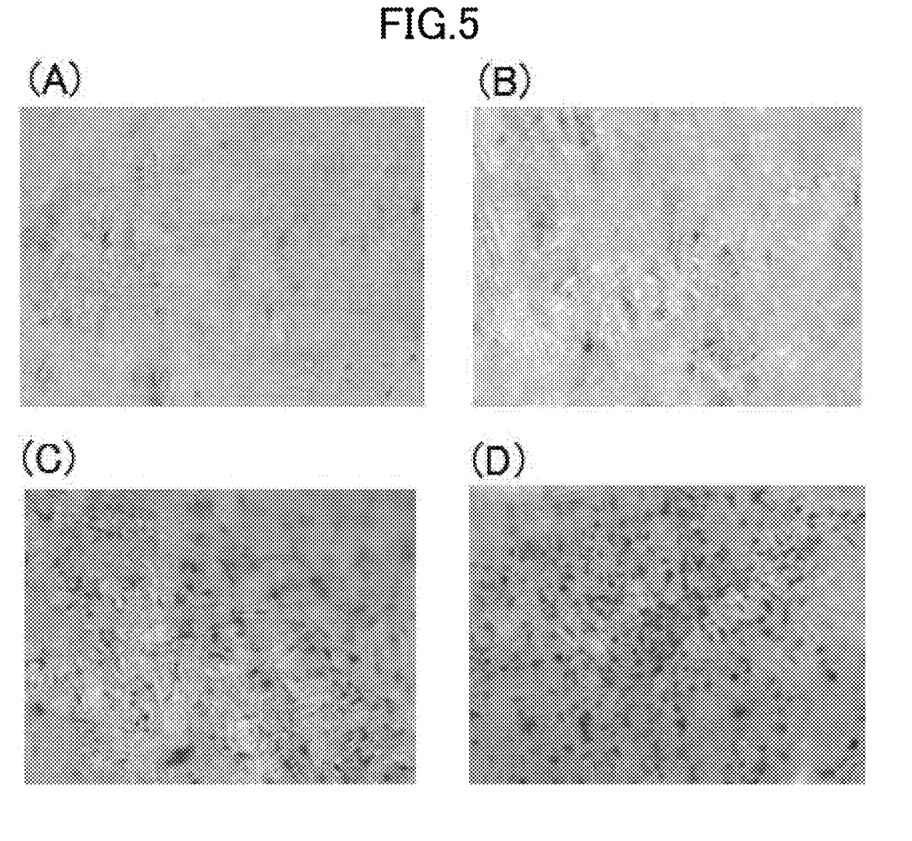
FIG. 5 contains photographs that each show a matrix from which cells were harvested by a cultured cell harvesting method according to Example 3. Photograph (A) shows a case where an enzyme solution had a mixing ratio expressed as trypsin-EDTA:collagenase:caseinase=2:2:2. Photograph (B) shows a case where an enzyme solution had a mixing ratio expressed as trypsin-EDTA:collagenase:caseinase=2:1:1. Photograph (C) shows a case where an enzyme solution had a mixing ratio expressed as trypsin-EDTA:collagenase:caseinase=0.5:2:2. Photograph (D) shows a case where an enzyme solution had a mixing ratio expressed as trypsin-EDTA:collagenase:caseinase=1:1:1.

Following a subsequent wash of the matrices in the bottle with PBS (−), the human adipose tissue-derived mesenchymal cells released from the matrices were harvested. The matrices were stained with crystal violet in the same manner as in Example 1, and photographed (FIG. 5(A)). The viability of the cells was 95.4%.

The treatments were performed in the same manner as described above except that an enzyme solution used in the enzyme treatment step had a mixing ratio expressed as trypsin-EDTA:collagenase:caseinase=2:1:1 (T2C1D1). The matrices were then photographed (FIG. 5(B)). Note that this mixing ratio is the same as that of photograph (A) of FIG. 3 showing the results of Example 2. The viability of the cells was 94.8%.

The treatments were performed in the same manner as described above except that an enzyme solution used in the enzyme treatment step had a mixing ratio expressed as trypsin-EDTA:collagenase:caseinase=0.5:2:2 (T0.5C2D2). The matrices were then photographed (FIG. 5(C)). The viability of the cells was 96.2%.

The treatments were performed in the same manner as described above except that an enzyme solution used in the enzyme treatment step had a mixing ratio expressed as trypsin-EDTA:collagenase:caseinase=1:1:1 (T1C1D1). The matrices were then photographed (FIG. 5(D)). The viability of the cells was 93.1%.

Figure 6:
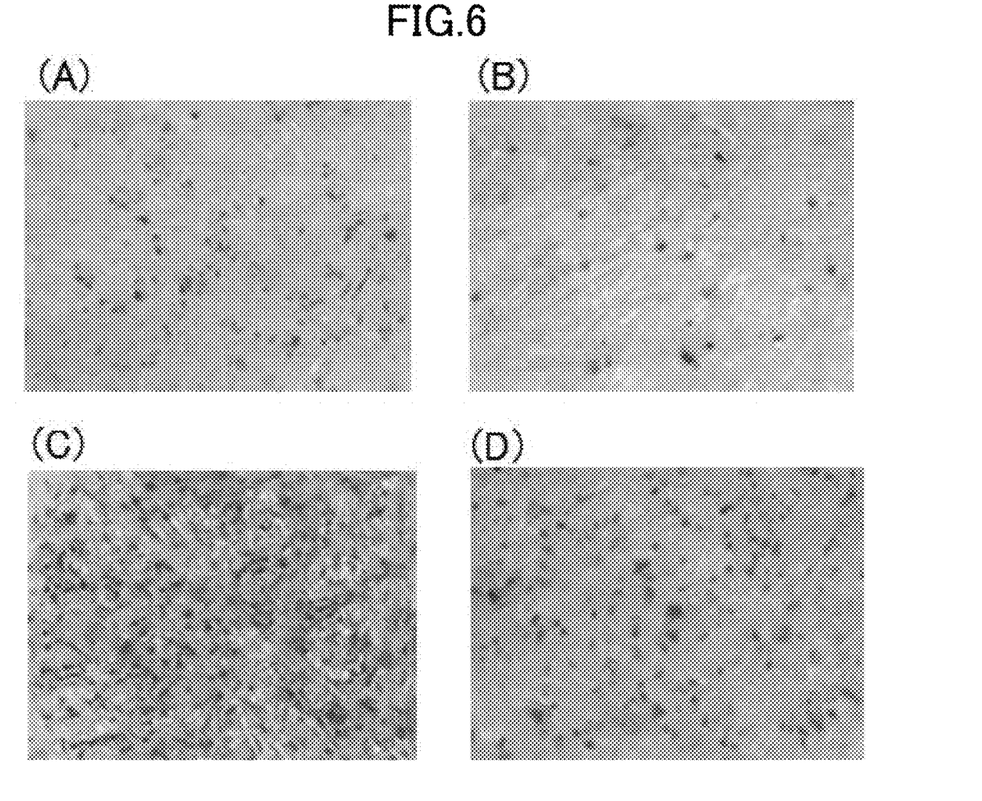
FIG. 6 contains photographs that each show a comparison between cell harvest rates resulting from a vibration treatment step performed by pipetting. Photograph (A) shows a case where an enzyme solution had a mixing ratio expressed as trypsin-EDTA:collagenase:caseinase=2:2:2. Photograph (B) shows a case where an enzyme solution had a mixing ratio expressed as trypsin-EDTA:collagenase:caseinase=2:1:1. Photograph (C) shows a case where an enzyme solution had a mixing ratio expressed as trypsin-EDTA:collagenase:caseinase=0.5:2:2. Photograph (D) shows a case where an enzyme solution had a mixing ratio expressed as trypsin-EDTA:collagenase:caseinase=1:1:1.

As a reference example, a vibration treatment step was performed by pipetting. Specifically, cells were cultured in a bottle using the high-density cell culture system "BelloCell" of CESCO BIOENGINEERING CO., LTD., and then PBS (−) was added for a wash, in the same manner as in Example 1. The PBS (−) was removed. An enzyme solution in a minimum amount required to make all the matrices covered under the solution was added and an enzyme treatment was performed for 15 minutes at 37° C. The enzyme solution had a mixing ratio expressed as trypsin-EDTA:collagenase:caseinase=2:2:2 (T2C2D2). Thereafter, a vibration treatment was performed by pipetting with use of a Pasteur pipette. Following a subsequent wash of the matrices in the bottle with PBS (−), the human adipose tissue-derived mesenchymal cells released from the matrices were harvested. The matrices were stained with crystal violet in the same manner as in Example 1, and photographed (FIG. 6(A)). The viability of the cells was 99.1%.

The treatments were performed in the same manner as described above except that an enzyme solution used in the enzyme treatment step had a mixing ratio expressed as trypsin-EDTA:collagenase:caseinase=2:1:1 (T2C1D1). The matrices were then subjected to a vibration treatment by pipetting (FIG. 6(B)). The viability of the cells was 95.3%.

The treatments were performed in the same manner as described above except that an enzyme solution used in the enzyme treatment step had a mixing ratio expressed as trypsin-EDTA:collagenase:caseinase=0.5:2:2 (T0.5C2D2).

The vibration treatment was performed by pipetting (FIG. 6(C)). The viability of the cells was 85.5%.

The treatments were performed in the same manner as described above except that an enzyme solution used in the enzyme treatment step had a mixing ratio expressed as trypsin-EDTA:collagenase:caseinase=1:1:1 (T1C1D1). The vibration treatment was performed by pipetting (FIG. 6(D)). The viability of the cells was 90.5%.

Figure 7:
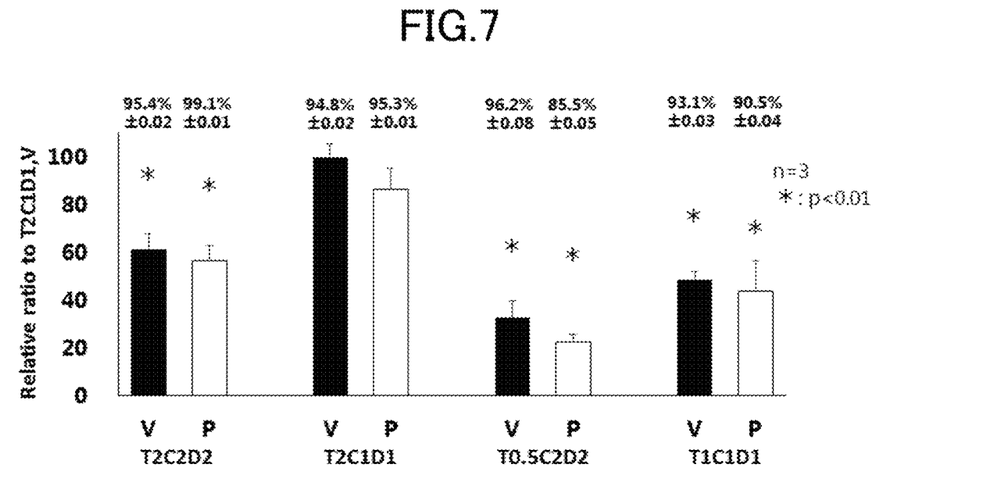
FIG. 7 shows a comparison between cell harvest rates resulting from enzyme solutions containing different ingredients.

FIG. 7 shows a comparison between the cell harvest rates of the case where the vibration treatment step is performed by a vortex mixer and the case where the vibration treatment step is performed by pipetting. In FIG. 7, the cell harvest rates are indicated by a relative value while the cell harvest in the case of using the enzyme solution of T2C1D1 and the vortex mixer is assumed to be 100.

The results of Example 3 have demonstrated that in the case of the normal culture period, the enzyme solution having a mixing ratio expressed as trypsin-EDTA:collagenase:caseinase=2:1:1 leads to the highest cell harvest rate.

(4) Example 4

In Example 4, studies were made on the mixing ratio of the enzyme solution that exhibits the highest harvest efficiency in the case of a long culture period, that is, on a mixture of trypsin-EDTA, collagenase, and caseinase.

Human adipose tissue-derived mesenchymal cells purchased from Lonza were used. The cells were cultured in a bottle-shaped culture bottle. The bottle had a volume of 1500 ml (100 mm in mouth diameter, 210 mm in height, and 110 mm in bottom diameter). The culture bottle was filled with matrices comprised of a culture solution and a nonwoven fabric of a polymer material. The human adipose tissue-derived mesenchymal cells were inoculated into the matrices. The cells were cultured for 25 days following the inoculation, while aeration and nutrition for the cells and excretion of metabolites ($CO_2$) took place. Then, PBS (−) was added for a wash.

The PBS (−) was reoved. An enzyme solution was added and the enzyme treatment was performed for 15 minutes at 37° C. The enzyme solution had a mixing ratio expressed as trypsin-EDTA:collagenase:caseinase=2:4:4 (T2C4D4).

Thereafter, a vibration treatment was provided, using a vortex mixer (at 2,800-3,200 rpm, for 30 seconds, with the vessel bottom surface kept in contact with the mixer). Specifically, the culture bottle containing cells subjected to the enzyme treatment was placed on a rubber platform of the vortex mixer, and a vertical vibration was applied to the enzyme-treated cultured cells, thereby performing a vibration treatment. Thereafter, the bottle was gently shaken in a vertical direction manually, and another vibration treatment was provided using the vortex mixer (at 2,800-3,200 rpm, for 30 seconds, with the vessel bottom surface kept in contact with the mixer).

Figure 8:
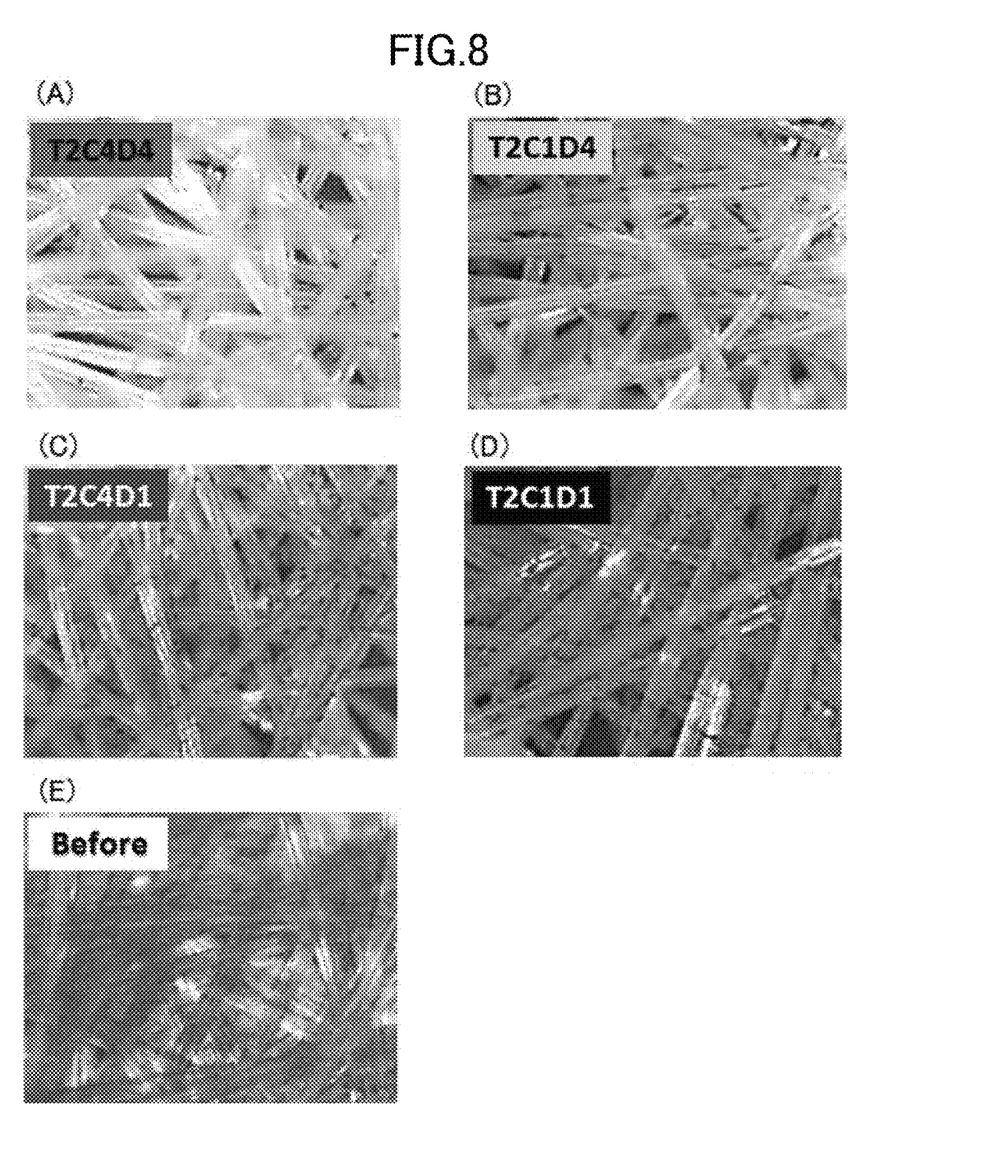
FIG. 8 contains photographs that each show a matrix from which cells were harvested by a cultured cell harvesting method according to Example 4. Photograph (A) shows a case where an enzyme solution had a mixing ratio expressed as trypsin-EDTA:collagenase:caseinase=2:4:4. Photograph (B) shows a case where an enzyme solution had a mixing ratio expressed as trypsin-EDTA:collagenase:caseinase=2:1:4. Photograph (C) shows a case where an enzyme solution had a mixing ratio expressed as trypsin-EDTA:collagenase:caseinase=2:4:1. Photograph (D) shows a case where an enzyme solution had a mixing ratio expressed as trypsin-EDTA:collagenase:caseinase=2:1:1. Photograph (E) shows a comparative example in which no enzyme treatment was provided.

Following a subsequent wash of the matrices in the bottle with PBS (−), the human adipose tissue-derived mesenchymal cells released from the matrices were harvested. After staining with crystal violet, the matrices were photographed (FIG. 8(A)). The viability of the cells was 96.3%.

The treatments were performed in the same manner as described above except that an enzyme solution used in the enzyme treatment step had a mixing ratio expressed as trypsin-EDTA:collagenase:caseinase=2:1:4 (T2C1D4). The matrices were stained with crystal violet and then photographed (FIG. 8(B)). The viability of the cells was 97.2%.

The treatments were performed in the same manner as described above except that an enzyme solution used in the enzyme treatment step had a mixing ratio expressed as trypsin-EDTA:collagenase:caseinase=2:4:1 (T2C4D1). The matrices were stained with crystal violet and then photographed (FIG. 8(C)). The viability of the cells was 97.7%.

The treatments were performed in the same manner as described above except that an enzyme solution used in the enzyme treatment step had a mixing ratio expressed as trypsin-EDTA:collagenase:caseinase=2:1:1 (T2C1D1). The matrices were stained with crystal violet and then photographed (FIG. 8(D)). The viability of the cells was 96.0%.

Figure 9:
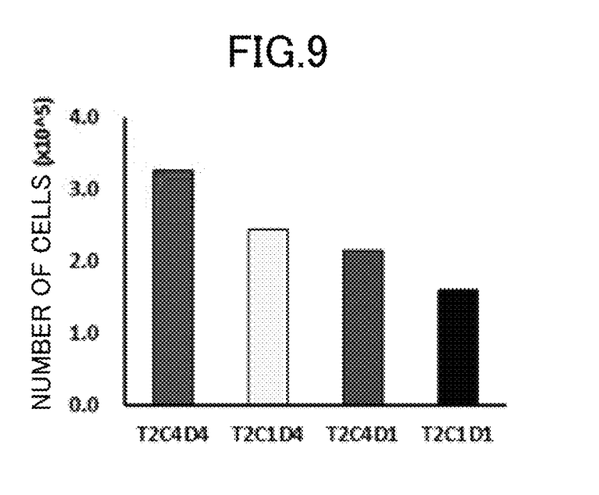
FIG. 9 is a graph showing the numbers of cells harvested by the cultured cell harvesting method according to Example 4.

A comparative example was prepared as follows. Human adipose tissue-derived mesenchymal cells were inoculated into a culture bottle filled with matrices comprised of a culture medium and a nonwoven fabric of a polymer material. The cells were cultured for 25 days following the inoculation, and then PBS (−) was added for a wash. The matrices before being subjected to an enzyme treatment were photographed (FIG. 8(E)). With reference to FIG. 8(E), a large number of human adipose tissue-derived mesenchymal cells remained adhering to the matrices. With reference to FIG. 8(A), almost no human adipose tissue-derived mesenchymal cells were found to adhere to the matrices. The numbers of human adipose tissue-derived mesenchymal cells adhering to the matrices descended in the order of FIG. 8(A), FIG. 8(B), FIG. 8(C), and FIG. 8(D). FIG. 9 shows the numbers of cells harvested in the cases of using enzyme solutions having mixing ratios of T2C4D4, T2C1D4, T2C4D1, and T2C1D1, respectively. As shown in FIG. 9, the numbers of cells harvested descended in the order of T2C4D4, T2C1D4, T2C4D1, and T2C1D1. The results of this experiment have demonstrated that in the case of the long culture period, use of the enzyme solution having a mixing ratio expressed as trypsin-EDTA:collagenase:caseinase=2:4:4 (T2C4D4) in the enzyme treatment step leads to the highest cell harvest rate.

The method of the present invention is useful for harvesting, from a scaffold, cells which have been cultured in large scale.

The invention claimed is:

1. A method for harvesting cultured cells from a three-dimensional porous scaffold, the method comprising the steps of:
   culturing cells in the three-dimensional porous scaffold sealed in a culture vessel having a flat bottom surface;
   providing an enzyme treatment on the cultured cells in the culture vessel, the enzyme treatment performed by adding an enzyme solution containing trypsin-EDTA, collagenase, and caseinase into the culture vessel; and
   providing a vibration treatment on the cultured cells, the vibration treatment being performed by bringing the flat bottom surface of the culture vessel, into which the enzyme solution has been added, into only surface contact with a single platform, the single platform being non-fixedly connected to the culture vessel, the single platform being provided at a position offset with respect to a center of a drive shaft of a vortex mixer and making a motion in a horizontal plane so that a vertical vibration is applied to the cultured cells subjected to the enzyme treatment with minimization of occurrence of a swirling flow, thereby releasing the cultured cells from the three-dimensional porous scaffold,
   wherein the enzyme solution in the step of providing the enzyme treatment has a mixing ratio expressed as trypsin-EDTA:collagenase:caseinase=0.25 to 2.0:1 to 6:3.33 to 20, where each numeric value is expressed in units of mg/mL.

2. The method of claim 1, wherein, in a case in which a cell culture period in the step of culturing is 5 to 14 days, the enzyme solution in the step of providing the enzyme treatment has a mixing ratio expressed as trypsin-EDTA:collagenase:caseinase 0.25 to 1.0:1 to 2:3.33 to 6.66, where each numeric value is expressed in units of mg/mL.

3. The method of claim 1, wherein, in a case in which a cell culture period in the step of culturing is 15 to 30 days, the enzyme solution in the step of providing the enzyme treatment has a mixing ratio expressed as trypsin-EDTA:collagenase:caseinase=1.0 to 2.0:1 to 6:6.66 to 20, where each numeric value is expressed in units of mg/mL.

4. The method of claim 2, wherein the platform makes the motion in the horizontal plane at a frequency of 20 Hz to 100 Hz.

5. The method of claim 3, wherein the platform makes the motion in the horizontal plane at a frequency of 20 Hz to 100 Hz.

6. The method of claim 2, wherein the cells are ES cells, iPS cells, or adult stem cells.

7. The method of claim 3, wherein the cells are ES cells, iPS cells, or adult stem cells.

8. The method of claim 2, wherein the three-dimensional porous scaffold has an average porosity of 80% or more and an average pore size of 10 μm to 800 μm.

9. The method of claim 3, wherein the three-dimensional porous scaffold has an average porosity of 80% or more and an average pore size of 10 μm to 800 μm.

10. The method of claim 2, wherein the three-dimensional porous scaffold has a culture area of 800 $cm^2$ to 900000 $cm^2$.

11. The method of claim 3, wherein the three-dimensional porous scaffold has a culture area of 800 $cm^2$ to 900000 $cm^2$.

\* \* \* \* \*